(12) United States Patent
Deinzer et al.

(10) Patent No.: US 7,817,772 B2
(45) Date of Patent: Oct. 19, 2010

(54) METHOD FOR DETERMINING PRESENCE DISTRIBUTIONS WITH LOCAL THREE-DIMENSIONAL RESOLUTION FOR A SUBSTANCE IN A VASCULAR SYSTEM AND CORRESPONDING FACILITIES

(75) Inventors: Frank Deinzer, Röthenbach (DE); Esther-Sabrina Platzer, Jena (DE)

(73) Assignee: Siemens Aktiengesellschaft, Munich (DE)

( * ) Notice: Subject to any disclaimer, the term of this patent is extended or adjusted under 35 U.S.C. 154(b) by 225 days.

(21) Appl. No.: 12/154,310

(22) Filed: May 22, 2008

(65) Prior Publication Data

US 2008/0292047 A1 Nov. 27, 2008

(30) Foreign Application Priority Data

May 25, 2007 (DE) .................... 10 2007 024 451

(51) Int. Cl.
*A61B 6/00* (2006.01)
(52) U.S. Cl. .......................................... 378/4
(58) Field of Classification Search .......... 378/4, 378/98.11
See application file for complete search history.

(56) References Cited

U.S. PATENT DOCUMENTS

| | | | |
|---|---|---|---|
| 6,442,235 B2* | 8/2002 | Koppe et al. ............... 378/62 |
| 6,512,807 B1* | 1/2003 | Pohlman et al. ............. 378/4 |
| 6,795,524 B2* | 9/2004 | Hayashi ................. 378/98.12 |
| 2002/0041654 A1* | 4/2002 | Hayashi .................... 378/196 |
| 2002/0123680 A1* | 9/2002 | Vaillant et al. ............. 600/407 |
| 2002/0136440 A1 | 9/2002 | Yim et al. |
| 2003/0040669 A1* | 2/2003 | Grass et al. ............... 600/407 |
| 2003/0128801 A1 | 7/2003 | Eisenberg et al. |
| 2004/0066958 A1* | 4/2004 | Chen et al. ................ 382/128 |
| 2004/0111023 A1* | 6/2004 | Edic et al. ................. 600/425 |
| 2006/0058638 A1 | 3/2006 | Boese et al. |
| 2006/0188138 A1* | 8/2006 | Kohler et al. ............. 382/130 |
| 2006/0215815 A1* | 9/2006 | Rasche ...................... 378/95 |

(Continued)

FOREIGN PATENT DOCUMENTS

DE 10 2004 018 499 A1 6/2005

OTHER PUBLICATIONS

Platzer et al., 3D Blood Flow Reconstruction from 2D Angiograms, Bildverarbeitung fur die Medizin, 2008, pp. 288-292.*

(Continued)

*Primary Examiner*—Edward J Glick
*Assistant Examiner*—Alexander H Taningco

(57) ABSTRACT

A computer receives a volume data set describing a vascular system with local three-dimensional resolution and a temporal sequence of groups of x-ray images. An acquisition time is assigned to each group of x-ray images comprising at least one x-ray image. Each x-ray image shows an actual presence distribution with local two-dimensional resolution for a substance in the vascular system, as defined at the respective acquisition time. The computer uses an initial presence distribution with local three-dimensional resolution for the substance, as defined for a start time, to determine further presence distributions with local three-dimensional resolution for the substance automatically for determination times by iterative resolution of fluid dynamics movement equations, which are per se location-independent. It automatically corrects the further presence distributions, if their respective determination time corresponds to one of the acquisition times, based on the temporally corresponding group of x-ray images.

16 Claims, 6 Drawing Sheets

U.S. PATENT DOCUMENTS

2007/0083105 A1* 4/2007 Miyazaki et al. ............ 600/410
2008/0192887 A1* 8/2008 Weese et al. .................. 378/41

OTHER PUBLICATIONS

Doucet et al., Sequetial Monte Carlo Methods in Practice, Springer-Verlag, 2001, pp. 1-6.*
Sanjeev et al., A Tutorial on Particle Filters for Online Nonlinear/Non-Gaussian Bayesian Tracking, IEEE Transactions on Signal Processing, vol. 50., No. 2, Feb. 2002, pp. 174-188.*
T. Patrila, D. Trif, "Basics of Fluid Mechanics and Introduction to Computational Fluid Dynamics, Numerical Methods and Algorithms", Springer-Verlag, 2005.
S. Arulampalam, S. Maskell, N. Gordon, "A Tutorial on particle Filters for On-Line Nonlinear/Non-Gaussian Bayesian Tracking", IEEE Transactions on Signal Processing, vol. No. 2, pp. 174-188, 2002, Abstract.
A. Doucet, N. De Freitas, N. Gordon, "Sequential Monte Carlo Methods in Practice", Springer-Verlag, 2001.
Esther-Sabrina Platzer; Visualisierung von Blutfluss im 3-D aus 2-D-Angiogrammen; Platzer; Diplomarbeit, Universität Koblenz-Landau und Siemens Medical Solutions Forchheim, Aug. 2006 http://www.uni-koblenz.de/FB4/Publications/Theses/ShowThesis?id=1893#ref1 vorr. nicht veröffentlicht; Others; 2006.
H. Schmitt, M. Grass, V. Rasche, O. Schramm, S. Haehnel, K. Sartor; An X-Ray-Based Method for the Determination of the Contrast Agent Propagation in 3-D Vessel Structures; Schmitt et al.; IEEE Transactions on Medical Imaging, vol. 21, No. 3, pp. 251-262, März 2002; Magazine; 2002.
H. Schmitt et al.; Reconstruction of blood propagation in three-dimensional rotational X-ray angiography (3D-RA) Schmitt et al.; Computerized Medical Imaging and Graphics, Oct. 2005; vol. 29(7), pp. 507-520, Epub Sep. 2, 2005.; Magazine; 2005.
Alvaro Soto; Self Adaptive Particle Filter Soto; 19. IJCAI 2005: Edinburgh, Scotland, UK Leslie Pack Kaelbling, Alessandro Saffiotti (Eds.): Proceedings of the 19th International Joint Conference on Artificial Intelligence, Edinburgh, Scotland, UK, Jul. 30-Aug. 5, 2005, pp. 1398-1406, 2005.
Wikipedia "Kontrastmittel" vom Feb. 21, 2006, S. 1-3 + Bibliographie http://web.archive.org/web/20060221083907 http://de.wikipedia.org/wiki/Kontrastmittel; Others; 2006.
Kyongtae T. Bae, MD, PhD: "Peak Contrast Enhancement in CT and MR Angiography: When Does it Occur and Why? Pharmacokinetic Study in a Porcine Model"; Radiology 2003, vol. 227, No. 3: pp. 809-816 http://wikipedia.org/wiki/Computational fluid dynamics; Others; 2003.
"Computational fluid dynamics (CFD)" (is the use of computers to analyze problems in fluid dynamics) Aug. 30, 2006, pp. 1-7 + Search Result http://en.wikipedia.org/wiki/computational_fluid_dynamics http://web.archive.org/web/20060830182519/; Others; 2006.

* cited by examiner

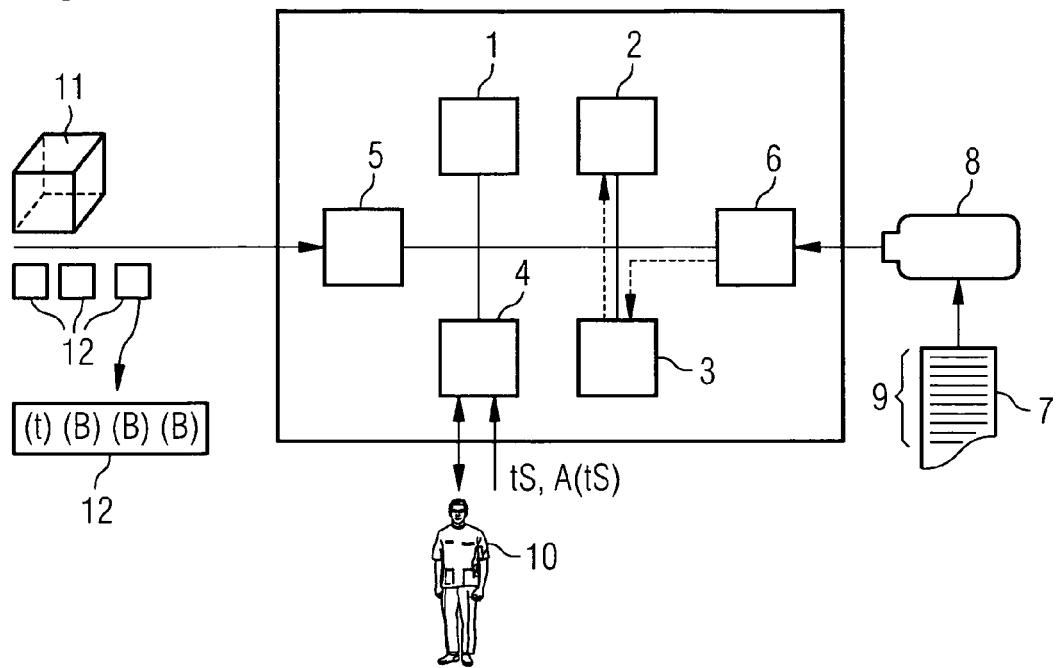
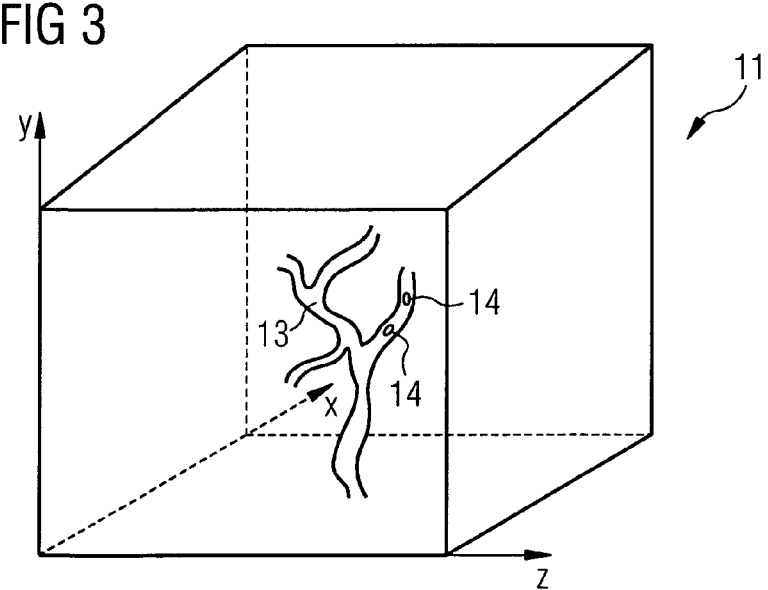

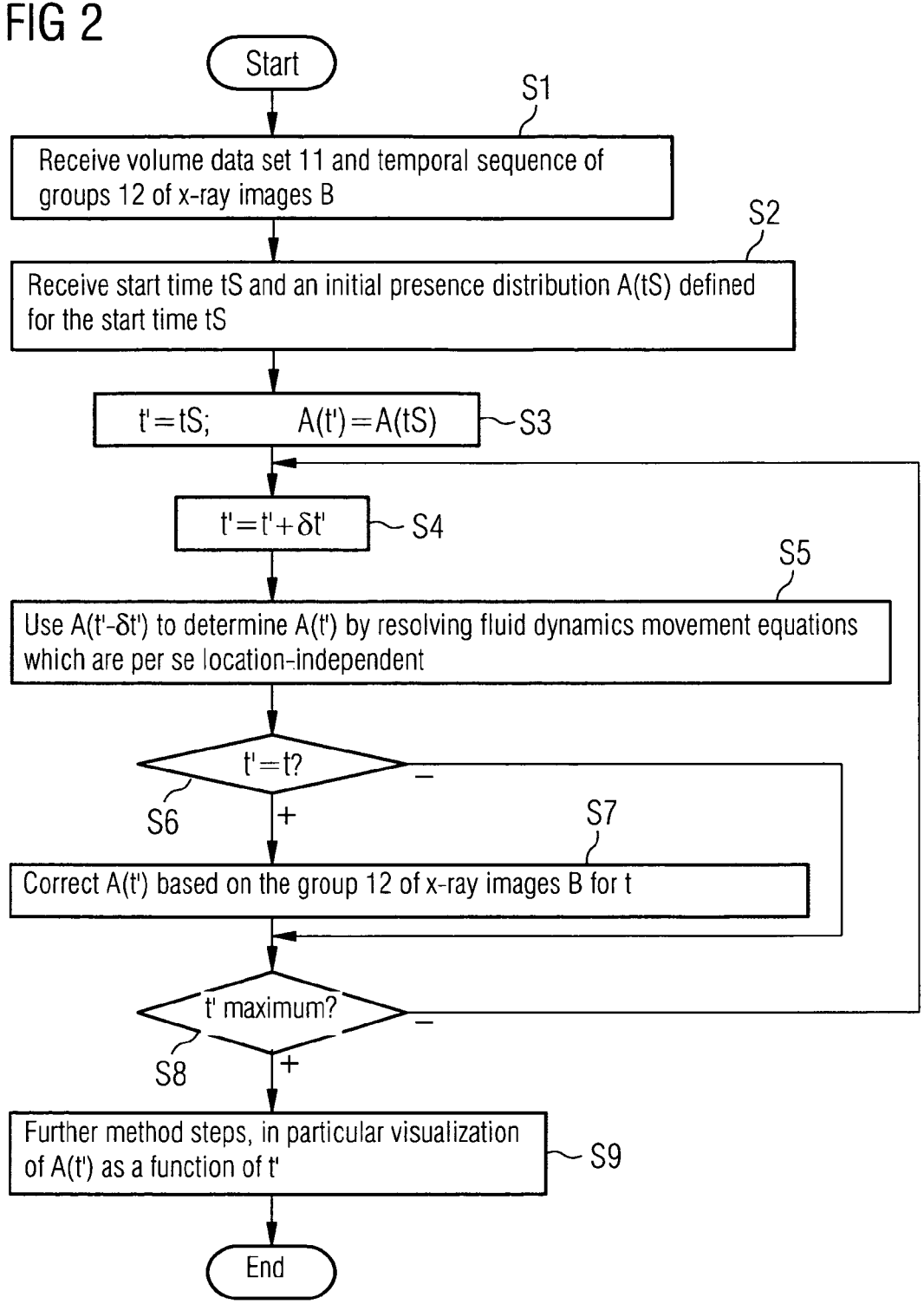

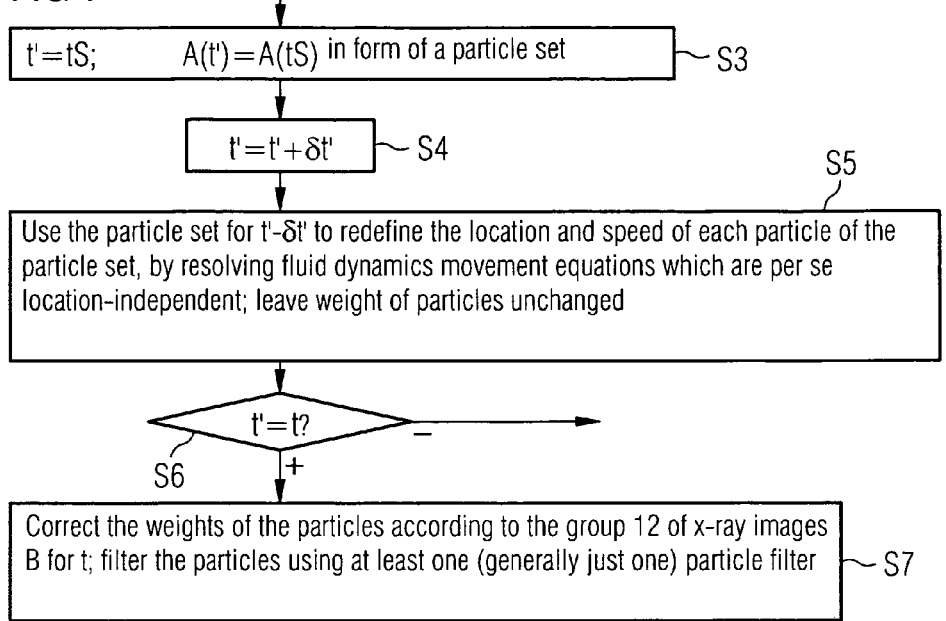
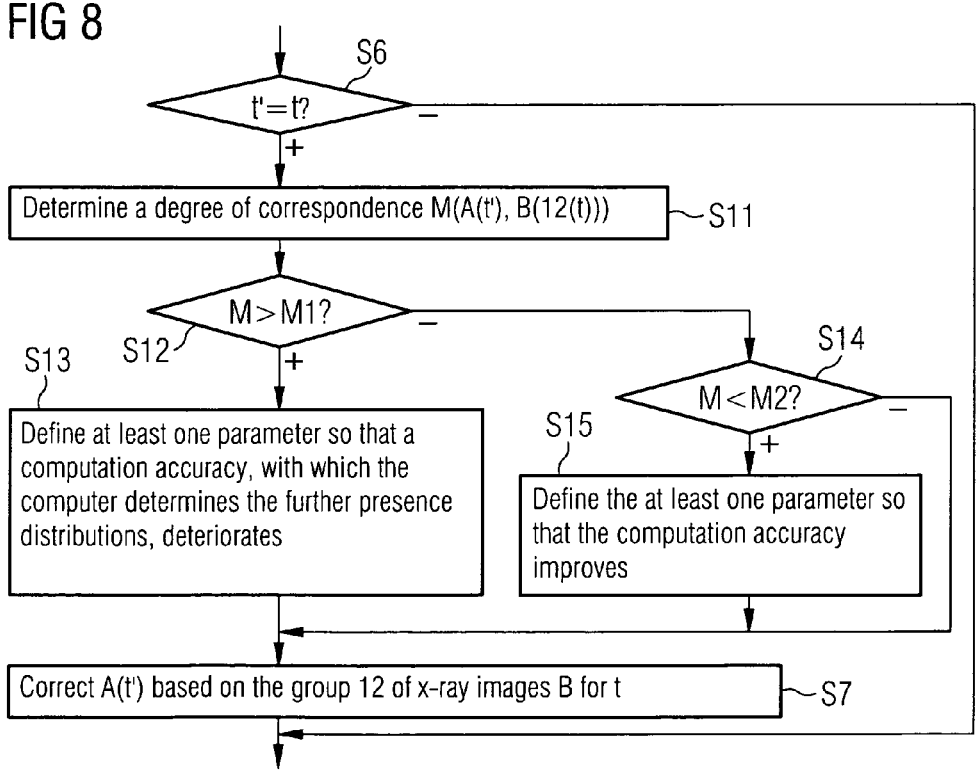

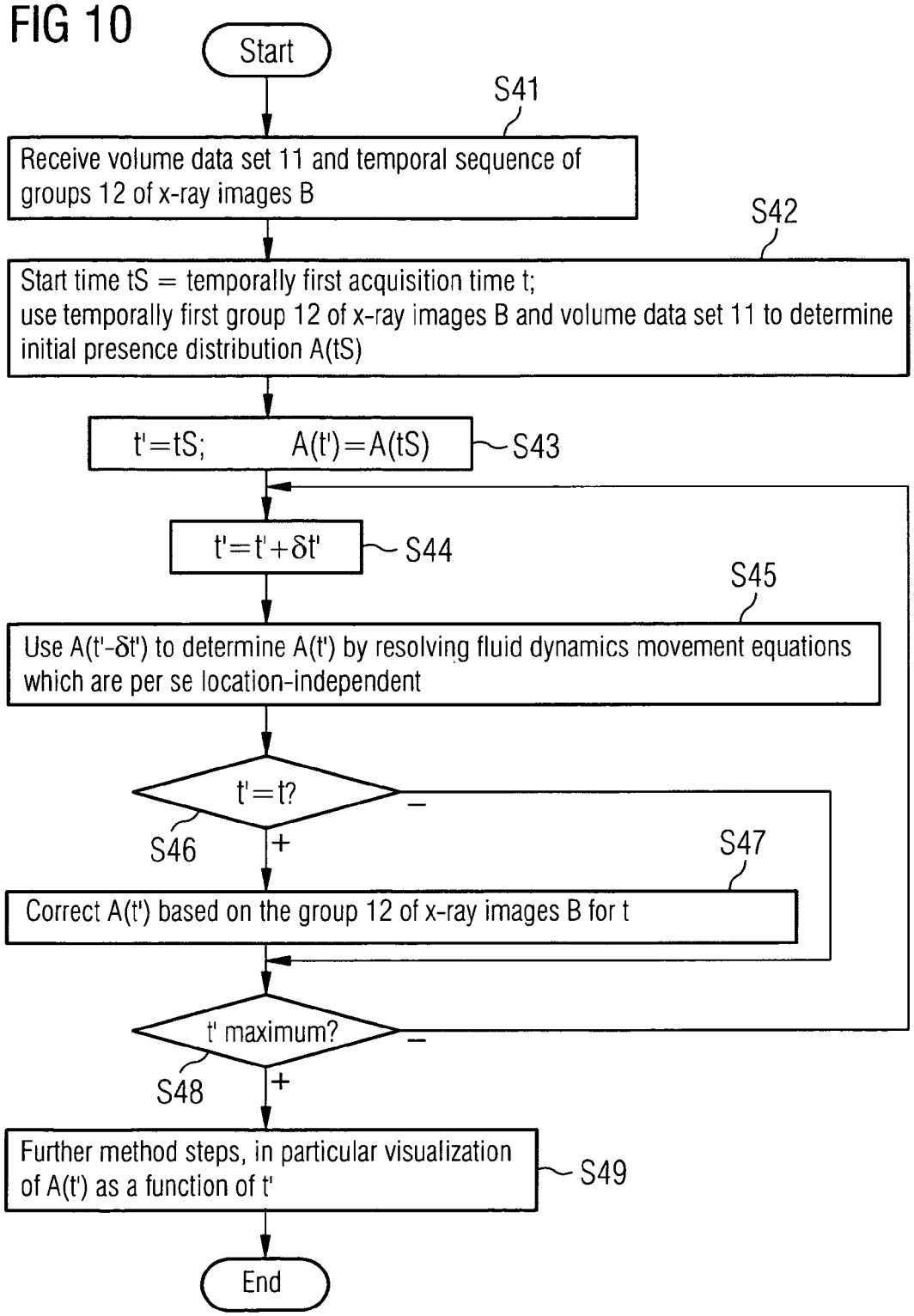

METHOD FOR DETERMINING PRESENCE DISTRIBUTIONS WITH LOCAL THREE-DIMENSIONAL RESOLUTION FOR A SUBSTANCE IN A VASCULAR SYSTEM AND CORRESPONDING FACILITIES

CROSS REFERENCE TO RELATED APPLICATIONS

This application claims priority of German application No. 10 2007 024 451.9 filed May 25, 2007, which is incorporated by reference herein in its entirety.

FIELD OF THE INVENTION

The present invention relates to a method for determining presence distributions with local three-dimensional resolution for a substance in a vascular system.

BACKGROUND OF THE INVENTION

Diagnosis of vascular diseases using three-dimensional imaging requires visualization of the blood flow through the corresponding vessels. Treatment generally takes place with minimal invasion using catheters, which are inserted into the corresponding blood vessel.

In order to be able to plan a minimally invasive intervention as precisely as possible and in particular to be able to carry it out exactly, the physician requires information about the position and spread of the vessels (location information) as well as the most accurate information possible about the blood flow through the corresponding vessel (temporal information). While aneurysms generally show up very clearly in the corresponding images, stenoses are generally relatively difficult to see. Instead the angiograms show points in the vessels where the through-flow of blood is much reduced. If stenosis leads to the complete occlusion of a vessel, this means that the corresponding vessel and all the vessels supplied by it are no longer identifiable in the x-ray recording. The three-dimensional visualization of the blood flow therefore provides the physician with important information about the degree of constriction or widening of a vessel and any possible effect on other vessels.

In a clinical situation the diagnosis of vascular diseases is currently based on temporal two-dimensional angiography sequences (showing the blood flow) or static three-dimensional data sets, which generally show a completely filled vessel tree.

It is of considerable advantage if the temporally dynamic blood flow is known in the three-dimensional as well as the two-dimensional. To determine the blood flow in the three-dimensional volume, various approaches are known in the prior art.

A first approach consists of simulating the blood flow in the three-dimensional volume. These simulations operate without observing a true flow. Therefore it is a pure simulation. Only the three-dimensional volume data set is required for the simulation. In the context of the simulation, the flow movement through the vessels is calculated based on physical laws. The simulation is based on the Navier-Stokes equations, which allow a numerical approximation of so-called reactive flows. The Navier-Stokes equations form a complex of differential equations, which represents the laws of physics. Essentially they are based on the conservation equations for mass, momentum, energy and in some instances rotational momentum. During the simulation the viscosity and density of the blood are taken into account as are the influences of external pressure on the vessel. This type of simulation is known to those skilled in the art as computational fluid dynamics (abbreviated to CFD). By applying the Navier-Stokes equations to a specific vascular system it is possible to achieve a physically correct simulation of the blood flow, subject to sufficiently precise calculation and adequate information about the vascular system and other ambient conditions.

The overall complex of Navier-Stokes equations in conjunction with flow simulation is described for example in T. Petrila, D. Trif, "Basics of Fluid Mechanics and Introduction to Computational Fluid Dynamics, Numerical Methods and Algorithms", Springer-Verlag, 2005.

The procedure described to date is based on the real three-dimensional volume data set. However it represents a pure simulation in respect of the temporal dynamics of the blood flow. There is no feeding back to reality.

In another known procedure only two-dimensional images are used. Here two-dimensional angiography sequences are generated from a view with constant C-arm alignment as a contrast agent is briefly injected. The angiography sequences show the temporal propagation of the contrast agent through the required vessels. Generally a reference image without contrast agent is acquired at the start of the sequence and this is subtracted from all subsequent recordings in the sequence, in order to see only the part of the vessel tree filled with contrast agent in the images. The method is also known as digital subtraction angiography (DSA). However the two-dimensional angiography sequences only supply information with local two-dimensional resolution, not information with spatial (=local three-dimensional) resolution.

DE 10 2004 018 499 A1 discloses a determination method of the type mentioned in the introduction. With this method the computer uses the group of x-ray images assigned to the respective acquisition time and the volume data set to determine a respective possible presence distribution for each acquisition time. The computer also uses the temporal sequence of the presence distributions and a vascular structure of the vascular system to determine a final presence distribution for each acquisition time.

In some instance it is possible to use the procedure known from DE 10 2004 018 499 A1 to map the blood flow correctly from the two-dimensional to the three-dimensional. The procedure from DE 10 2004 018 499 A1 therefore already has significant advantages compared with the locally purely two-dimensional processing of the angiography sequence.

SUMMARY OF THE INVENTION

The object of the present invention is to create possibilities for determining the final presence distributions with local three-dimensional resolution for the substance with a high level of quality and in particular in a medically meaningful manner.

The object is achieved by the features of the claims.

According to the invention, a computer receives a volume data set and a temporal sequence of groups of x-ray images. The volume data set describes the vascular system with local three-dimensional resolution. An acquisition time is assigned to each group of x-ray images. Each group comprises at least one x-ray image and each x-ray image represents an actual presence distribution with local two-dimensional resolution for the substance in the vascular system present, as defined at the respective acquisition time.

According to the invention the computer uses an initial presence distribution defined for a start time to determine further presence distributions automatically by iterative resolution of fluid dynamics movement equations, which are per se location-independent, for determination times. If the respective determination time corresponds to one of the acquisition times, the computer automatically corrects the further presence distributions based on the temporally corresponding group of x-ray images.

In the context of the present invention the procedure known from simulation technology (key word: resolution of fluid dynamics movement equations) is used as the basis for the temporal updating of presence distributions. These presence distributions are however corrected based on the two-dimensional angiography sequences and/or aligned with these angiography sequences.

It is possible for the start time to correspond to the first acquisition time and for the computer to determine the initial presence distribution automatically based on the temporally first group of x-ray images and the volume data set. In many instances this procedure produces good results. It is however better if the computer receives the start time and the initial presence distribution in addition to the volume data set and the groups of x-ray images.

The difference between immediately consecutive determination times is preferably smaller than the difference between immediately consecutive acquisition times. This procedure allows the advantages of simulation, such as high computation and resolution accuracy for example, to be utilized, while on the other hand keeping a patient's x-ray exposure low.

For the same reasons it is preferable for the computer to determine the further presence distributions with a local accuracy, which is greater than a mapping accuracy with which the x-ray images can be back-projected into the volume data set.

In a further preferred embodiment provision is made for the computer to determine a degree of correspondence of at least one further presence distribution with the temporally corresponding group of x-ray images, to redefine at least one parameter as a function of the degree of correspondence, with the at least one parameter influencing a computation accuracy, with which the computer determines the further presence distributions, and to determine at least the further presence distributions temporally following the at least one further presence distribution taking into account the at least one redefined parameter.

This procedure has the advantage that the computation outlay required to determine the further presence distributions can be tailored to the possibilities for checking and correcting the angiography sequence.

It is possible for the computer to determine only the temporally following further presence distributions taking into account the at least one redefined parameter. However the computer preferably also determines already determined further presence distributions again taking into account the at least one redefined parameter.

The redefined parameter can vary in nature. For example it can be a difference between immediately consecutive determination times, a local accuracy with which the computer determines the further presence distributions and/or an accuracy of the movement equations per se.

In a further preferred embodiment the initial presence distribution and the further presence distributions are embodied as particle sets. This procedure allows the computation outlay required to determine the presence distributions to be minimized. If the initial presence distribution and the further presence distributions are embodied as particle sets, the computer determines the correction of the further presence distributions by filtering using at least (generally just) one particle filter.

If particle sets and particle filters are used and the parameter influencing computation accuracy is also redefined, the at least one redefined parameter can also be a variation of the particle sets and/or a variation of the particle filter.

BRIEF DESCRIPTION OF THE DRAWINGS

Further advantages and details will emerge from the description which follows of exemplary embodiments in conjunction with the drawings, in which essentially:

FIG. 1 shows a schematic diagram of the structure of a processing arrangement,
FIG. 2 shows a flow diagram,
FIG. 3 shows a volume data set,
FIG. 6 shows a diagram of a volume data set and an x-ray image and
FIGS. 7 to 10 show flow diagrams.

DETAILED DESCRIPTION OF THE INVENTION

Figure 4:
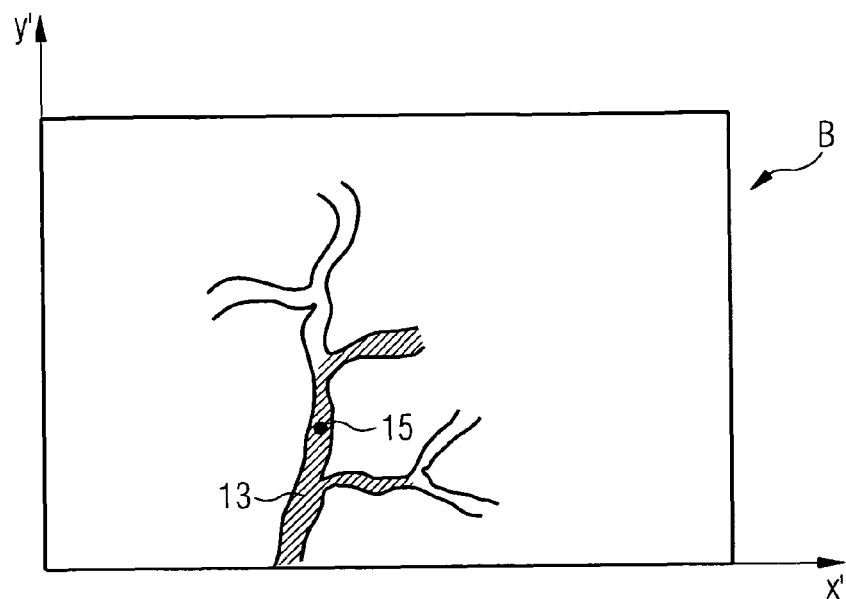
FIG. 4 shows an x-ray image.

In FIG. 1 a computer has standard components 1 to 6. In particular the computer has a microprocessor 1, a main memory (RAM) 2, a mass storage device 3 (for example a hard disk), a user interface 4, a data interface 5 and a programming interface 6. The components 1 to 6 are configured in the usual manner and interact with each other in the usual manner. Thus for example the user interface 4 can comprise standard input and output facilities, such as a keyboard, mouse, display unit, etc. The data interface 5 can be an internet or LAN interface or a USB interface for example. An embodiment as a drive for a removable medium (for example a CD-ROM or DVD) is also possible. Similar embodiments are possible for the programming interface 6. In some instances the data interface 5 and programming interface 6 can be combined to form a common interface.

A computer program 7 is supplied to the computer by way of the programming interface 6. For example a data medium 8, on which the computer program 7 is stored in machine-readable form, can be connected to the computer. The computer program 7 is then read from the data medium 8 and copied to the mass storage device 3 of the computer and similarly stored there.

The computer program 7 contains machine code 9, in other words program instructions, which can be executed directly and immediately by the computer. The computer program 7 can be called up by a user 10 using standard input commands (for example a double mouse click). When the computer program 7 is called up, it is loaded into the main memory 2 of the computer and executed by the computer. Execution of the computer program 7 by the computer causes the computer to execute a determination method, which is described in detail below in conjunction with the further figures.

According to FIG. 2 in a step S1 the computer first receives a volume data set 11 and a temporal sequence of groups 12 of x-ray images B. According to FIG. 3 the volume data set 11 has three spatial coordinates x, y, z and therefore has local three-dimensional resolution. It describes a vascular system 13. In particular the volume data set 11 can be present as a binary volume data set 11. In this instance a binary value "ONE" is assigned to each location (x, y, z) in the volume data set 11, which is a component of the vascular system 13, with the value "ZERO" being assigned to the other locations (x, y, z) of the volume data set 11. The locations of the volume data set 11, which are components of the vascular system 13, are hereafter referred to as vascular locations 14.

According to FIG. 1 each group 12 of x-ray images B comprises at least one x-ray image B. According to FIG. 1 the groups 12 can however alternatively also comprise a number of x-ray images B. The x-ray images B can be native images. They are however preferably DSA images (DSA=digital subtraction angiography). According to FIG. 4 each x-ray image B of each group 12 is defined using two surface coordinates x', y', thus having local two-dimensional resolution. It represents a presence distribution of a substance (in the case of native images for example blood with contrast agent, in the case of DSA images contrast agent) in the vascular system 13.

According to FIG. 1 each group 12 is also assigned an acquisition time t, when the x-ray images B of the respective group 12 were acquired. The groups 12 of x-ray images B are generally acquired with temporal equidistance. However this is not mandatory. Each x-ray image B of each group 12 is related to the acquisition time t of the respective group 12.

The sequence of the groups 12 of x-ray images B represents a temporal profile of a presence distribution with two-dimensional resolution for the substance in the vascular system 13. Despite the fact that the groups 12 of x-ray images B have less location information than the volume data set 11, a temporal profile of a presence distribution with local three-dimensional resolution should be determined for the substance in the vascular system 13. The determination of this temporal profile is the subject matter of the present invention.

In a step S2 the computer receives a start time tS and an initial presence distribution A(tS) defined for the start time tS. This can be predetermined for example by the user 10.

In a step S3 the computer sets a determination time t' to the start time tS. In step S3 the computer also sets the presence distribution A(t') for the current determination time t' as equal to the initial presence distribution A(tS).

In a step S4 the computer increments the determination time t' by a time step $\delta t'$. Then in a step S5 the computer uses the presence distribution A(t'−$\delta t$) for the immediately preceding determination time t'−$\delta t$, to calculate the associated presence distribution A(t') by resolving fluid dynamics movement equations for the present determination time t'. The movement equations per se (i.e. their structures) are location independent here. The computer can in particular resolve the so-called Navier-Stokes equations, in other words equations with the form $$\rho \frac{\partial u}{\partial t'} + \rho(u \cdot \nabla)u = -\nabla \rho + \eta \Delta u + (\lambda + \eta)\nabla(\nabla \cdot u) + f \quad (1)$$

$\rho$ here stands for pressure, u is a speed vector, $\lambda$ and $\eta$ are the so-called material constants (viscosity). f is the volume force density. It includes gravitation.

In step S6 the computer checks whether the current determination time t' corresponds to one of the acquisition times t. If so, the computer executes a step S7. Otherwise it omits step S7.

In step S7 the computer corrects the presence distribution A(t') determined for the respective determination time t'. It carries out the correction based on the temporally corresponding group 12 of x-ray images B. To this end the computer can alternatively map the determined presence distribution A(t') into the x-ray images B and carry out the correction on the basis of the correspondences of the mapped presence distribution A(t') to the x-ray images B of the respective group 12. Alternatively the computer can back-project the x-ray images B of the respective group 12 into the volume data set 11 and carry out the correction based on the back-projections.

Both procedures are in principle equivalent. The mapping of the volume data set 11 into the x-ray images B or the back-projection of the x-ray images B into the volume data set 11 and the registration of the volume data set 11 in relation to the x-ray images B required for this are known per se to those skilled in the art and represent their normal practice.

In step S8 the computer checks whether the current determination time t' has already reached its maximum value. If not, the computer returns to step S4. Otherwise the computer passes to step S9, in which the computer executes further steps of the inventive method. In particular, as part of step 9, the computer can carry out a visualization of the determined presence distributions A(t'), in particular of their temporal profile.

Figure 5:
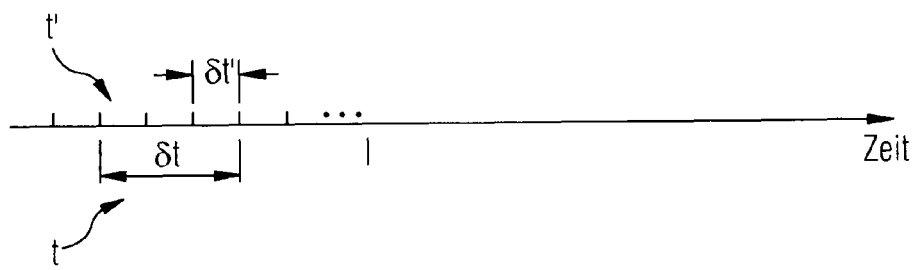
FIG. 5 shows a time diagram.

As mentioned above, both the determination times t' and the acquisition times t generally follow each other with mutual equidistance. The difference $\delta t'$ between temporally immediately consecutive determination times t' (i.e. the time step $\delta t'$) is therefore generally constant (see FIG. 5). Similarly the difference $\delta t$ between immediately consecutive acquisition times t is also constant. The time step $\delta t'$ of immediately consecutive determination times t' is however generally much smaller than the difference $\delta t$ between immediately consecutive acquisition times t. In particular the difference $\delta t$ between immediately consecutive acquisition times t generally corresponds to a whole-number multiple (e.g. twice, four times, etc.) of the time step $\delta t'$.

Figure 6:
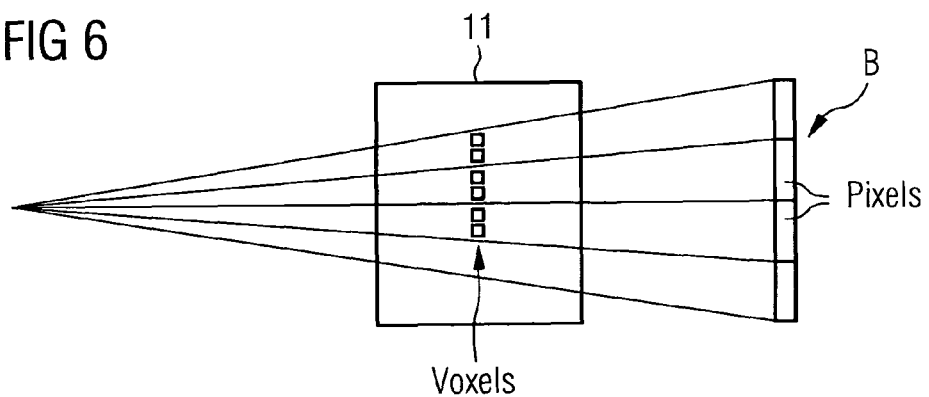

The pixels of the x-ray images B—see FIG. 6—have a certain expansion. The x-ray images B can only therefore be back-projected into the volume data set 11 with a limited mapping accuracy according to FIG. 6. The computer preferably determines the further presence distributions A(t') with a local accuracy which is greater than the mapping accuracy. For example the computer can determine the further presence distributions A(t') with a local accuracy that is twice, three times, four times, as high as the mapping accuracy. This is illustrated in FIG. 6 in that voxels of the volume data set 11 are shown smaller than the corresponding pixels of the x-ray images B.

In a preferred embodiment steps S3, S5 and S7 are implemented in the manner described below in conjunction with FIG. 7.

According to FIG. 7 in step S3 the computer sets the start state as a particle set. Each particle set contains a plurality of particles. The individual particles correspond respectively in this instance to a random sample. Each particle consists of a state vector in relation to the respective determination time t' and a weight, which expresses the probability that the respective particle will be present at a specified location (x, y, z) by the respective determination time t'. Further information is assigned to the particles, for example amount and direction of a speed, at which the respective particle moves.

The particle set is propagated temporally in step S5. The particles per se and their number remain unchanged in this process. However the location and speed (the latter according to amount and direction) of each particle are redetermined. The weight of the respective particle remains unchanged in the context of step S5.

In step S7 the weights of the particles are tailored correspondingly to the correspondence of the respective presence distribution A(t') to the x-ray images B of the respective group 12. If—in relation to an individual particle—the determined location of said particle and the locations 15 in the x-ray images B, at which substance is present (substance locations 15) coincide, the weight of the respective particle is increased. Otherwise the weight of the particle is reduced. However the weight remains greater than zero even if it is reduced. In step S7 according to FIG. 7 a filtering operation of at least one (generally just one) particle filter takes place. Filtering with the particle filter means that the particles are transferred onto the corrected presence distribution A(t') with a probability that is proportional to their new weight. Filtering with the particle filter means that the particles of the particle set (=presence distribution before correction) are thus transferred into the new particle set (=presence distribution after correction) in proportion to their new weight.

Particle filters per se are known to those skilled in the art. Reference is made by way of example to A. Doucet, N. de Freitas, N. Gordon, "Sequential Monte Carlo Methods in Practice", Springer-Verlag, 2001 and S. Arulampalam, S. Maskell, N. Gordon, "A Tutorial on Particle filters for On-line Nonlinear/Non-Gaussian Bayesian Tracking", IEEE Transactions on Signal Processing, vol. no. 2, pp 174-188, 2002.

An analytical resolution of the movement equations in step S5 is generally not possible. The movement equations are therefore generally discretized. For this reason in particular it is particularly advantageous to map the presence distributions A as particle sets, because particle filters necessarily imply a discrete procedure.

FIG. 8 shows a variant of FIG. 2. According to FIG. 8 steps S11 to S15 are secondary to step S6 and to step S7. According to FIG. 8 steps S11 to S15 are inserted between steps S6 and S7. Alternatively steps S11 to S15 could be made secondary to step S7.

In step S11 the computer determines a degree of correspondence M to the temporally corresponding group 12 of x-ray images B for at least one further presence distribution A(t')— generally the further presence distribution A(t') just determined.

In step S12 the computer compares the determined degree of correspondence M with an upper limit M1. If the degree of correspondence M exceeds the upper limit M1, the computer passes to step S13. In step S13 the computer redetermines at least one parameter. Determination is carried out so that a computation accuracy, with which the computer determines the further presence distributions A(t'), deteriorates. For example the computer can increase the time step δt' or reduce the local accuracy, with which it determines the further presence distributions A(t'). Alternatively or additionally the computer can reduce the accuracy of the movement equations per se. For example the computer can switch from compressible to non-compressible Navier-Stokes equations and/or ignore a physical component included in the movement equations. If the presence distributions A(t') are embodied as particle sets, the computer can alternatively or additionally also vary the particle sets (for example the number of particles) and/or the particle filters (for example the extent to which the weights are increased and/or reduced).

If the computer does not pass to step S13 from step S12, it moves to step S14. In step S14 the computer checks whether the degree of correspondence M is below a lower limit M2. If so, the computer passes to step S15. Step S15 is the inverse of step S13. Therefore the at least one parameter is redefined so that the computation accuracy improves.

If no further measures are taken, it can happen that the at least one parameter oscillates in a non-stable manner. Steps S11 to S15 are therefore preferably embodied so that previous values of the at least one parameter are taken into account. In particular when executing step S13 the previous value of the parameter can represent an upper accuracy limit and conversely when executing step S15 the previous value of the parameter can represent a lower accuracy limit.

The embodiment according to FIG. 8 means that the further presence distributions A(t') temporally following the currently determined further presence distribution A(t') are determined taking into account the at least one redefined parameter. This procedure is possible but not preferred. It is preferable to incorporate steps S11 to S15 in the determination method in FIG. 2 in the manner shown in FIG. 9. The procedure in FIG. 9 means that the computer also determines already determined further presence distributions A(t') again taking into account the at least one redefined parameter.

Figure 9:
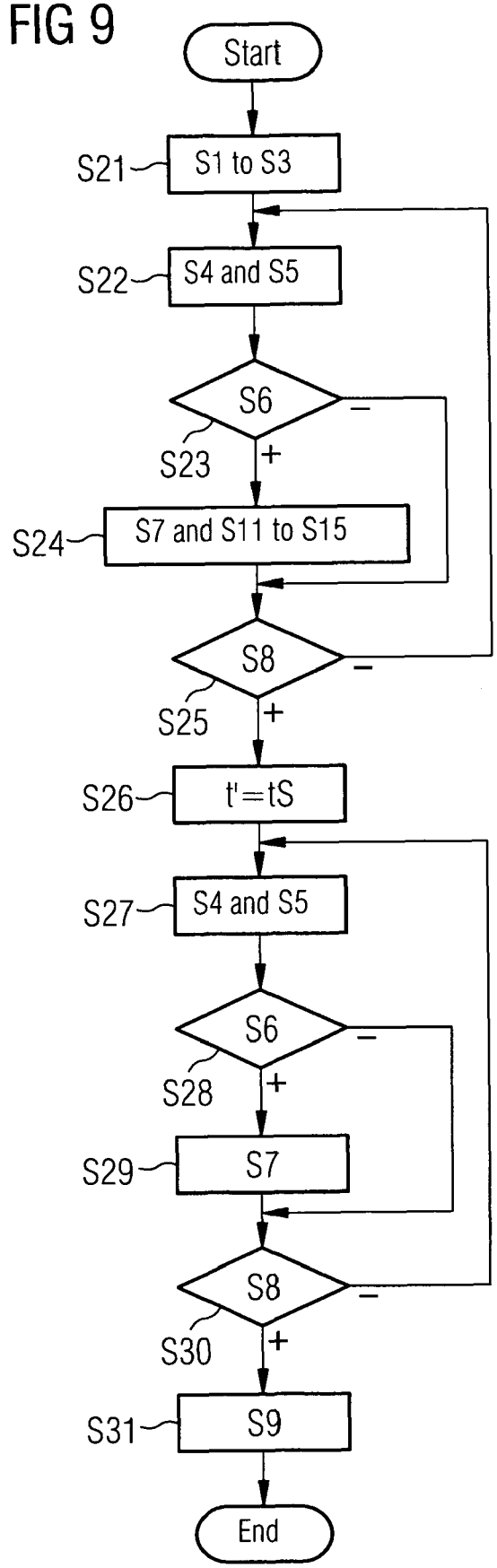

FIG. 9 shows steps S21 to S31. Steps S21 to S25 and S27 to S31 in FIG. 9 correspond to individual or several of the steps S1 to S9 and S11 to S15 described in conjunction with FIGS. 2 and 8. Therefore no detailed descriptions are necessary for steps S21 to S25 and S27 to S31. Step S26 is self-explanatory. No descriptions are therefore required for step 26 either.

FIG. 10 shows a modification of the determination method in FIG. 2. The modification according to FIG. 10 is also possible with the embodiments according to FIGS. 7 to 9.

FIG. 10 has steps S41 to S49, Steps S41 and S43 to S49 in FIG. 10 correspond here to steps S1 and S3 to S9 in FIG. 2. Therefore no detailed descriptions are necessary for steps S41 and S43 to S49. In step S42 the computer sets the start time tS as equal to the temporally first acquisition time t. As part of step S42 the computer also uses the temporally first group 12 of x-ray images B and the volume data set 11 to determine the initial presence distribution A(tS).

The present invention has many advantages. Some of these advantages are listed below.

For example the acquisition of the sequence of groups 12 of x-ray images B can take place with a larger difference δt than in the prior art.

The blood flow reconstruction is free of ambiguities.

Errors in the simulation (i.e. the resolution of the movement equations) can already be identified after only a few time steps δt', since the degree of correspondence M then becomes very small.

Calculation complexity during simulation can be tailored to the necessary and/or possible or desired accuracy.

Compared with heuristics-based procedures, in particular the combination of particle filters with integrated Navier-Stokes equations is more precise and has better mathematical/physical justification.

The simulation allows visual information to be obtained, which cannot be obtained by means of a purely heuristic analysis. This is true even if a back-projection into the volume data set 11 is effected in the prior art, because for example turbulence and other flow characteristics at the vessel walls and in the interior of the vessels can only be simulated and visualized by means of simulation.

The accuracy of the simulation can be controlled via the number of particles contained in the particle sets.

The above description serves solely to explain the present invention. The scope of protection of the present invention should however only be defined by the accompanying claims.

The invention claimed is:

1. A method for determining a presence distribution with a three-dimensional dataset for a substance in a vascular system of a patient, comprising:
    receiving a volume data set describing the vascular system with the three-dimensional dataset by a computer;
    receiving a sequence of groups of x-ray image locally acquired at a sequence of acquisition times by the computer, the x-ray image showing an actual presence distribution with a two-dimensional dataset for the substance in the vascular system at an acquisition time;
    assigning the acquisition times to the corresponding groups of the x-ray image by the computer;

defining a start time for an initial presence distribution by the computer;

simulating further presence distributions by iteratively resolving fluid dynamics movement equations for determination times from the initial presence distribution and the volume data set by the computer; and correcting the further presence distributions based on the corresponding groups of the x-ray image if the determination times correspond to the acquisition times by the computer.

2. The method as claimed in claim 1, wherein the start time is a first acquisition time of the sequence of the acquisition times.

3. The method as claimed in claim 2, wherein the initial presence distribution is calculated based on a corresponding first group of the groups of x-ray image and the volume data set.

4. The method as claimed in claim 1, wherein the start time and the initial presence distribution are received.

5. The method as claimed in claim 1, wherein a time interval between immediately consecutive determination times is smaller than a time interval between immediately consecutive acquisition times.

6. The method as claimed in claim 1, wherein the further presence distributions are determined with a local accuracy which is greater than a mapping accuracy.

7. The method as claimed in claim 6, wherein the x-ray image is back-projected into the volume data set based on the further presence distributions.

8. The method as claimed in claim 1, further comprising:
determining a degree of correspondence between one of the further presence distributions and the corresponding group of the x-ray image,
redefining a parameter that influences a computation accuracy as a function of the degree of correspondence, and
determining the further presence distributions based on the redefined parameter.

9. The method as claimed in claim 8, wherein the further presence distributions are determined again based on the redefined parameter.

10. The method as claimed in claim 8, wherein the parameter is selected from the group consisting of: a difference between immediately consecutive determination times, a local accuracy, and an accuracy of the fluid dynamics movement equations.

11. The method as claimed in claim 1, wherein the initial presence distribution and the further presence distributions comprise particle sets and the further presence distributions are corrected by filtering particles in the particle sets using a particle filter.

12. The method as claimed in claim 11, wherein the parameter is a variation of the particle sets or a variation of the particle filter.

13. The method as claimed in claim 1, wherein the further presence distributions are location-independent.

14. The method as claimed in claim 1, wherein the further presence distributions are automatically determined and corrected.

15. A data medium executed on a computer for determining a presence distribution with a local three-dimensional resolution for a substance in a vascular system of a patient, comprising:
a computer program that:
assigns acquisition times to a sequence of groups of x-ray image acquired at the acquisition times, the x-ray image showing an actual presence distribution with a local two-dimensional resolution for the substance in the vascular system at an acquisition time,
defines a start time for an initial presence distribution,
simulates further presence distributions by iteratively resolving fluid dynamics movement equations at for determination times based on the initial presence distribution and a volume data set describing the vascular system with the local three-dimensional resolution, and
corrects the further presence distributions based on the corresponding groups of the x-ray image if the determination times correspond to the acquisition times.

16. A computer for determining a presence distribution with a local three-dimensional resolution for a substance in a vascular system of a patient, comprising:
a storage device that stores:
a volume data set describing the vascular system with the local three-dimensional resolution, and
a sequence of groups of x-ray image acquired at a sequence of acquisition times, the x-ray image showing an actual presence distribution with a local two-dimensional resolution for the substance in the vascular system at an acquisition time; and
a processor that:
assigns the acquisition times to the corresponding groups of the x-ray image,
defines a start time for an initial presence distribution,
simulates further presence distributions by iteratively resolving fluid dynamics movement equations for determination times based on the initial presence distribution and the volume data set, and
corrects the further presence distributions based on the corresponding groups of the x-ray image if the determination times correspond to the acquisition times.

* * * * *